United States Patent
Schmid et al.

(10) Patent No.: US 10,894,884 B2
(45) Date of Patent: Jan. 19, 2021

(54) USE OF IRON OXIDE COATED ALUMINUM FLAKES HAVING RED 1st ORDER INTERFERENCE COLOR IN COATINGS

(71) Applicant: BASF SE, Ludwigshafen (DE)

(72) Inventors: Raimund Schmid, Neustadt (DE); Aron Wosylus, Bad Duerkheim (DE); Christoph Schwidetzky, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 341 days.

(21) Appl. No.: 15/740,864

(22) PCT Filed: Jun. 28, 2016

(86) PCT No.: PCT/EP2016/064993
§ 371 (c)(1),
(2) Date: Dec. 29, 2017

(87) PCT Pub. No.: WO2017/001393
PCT Pub. Date: Jan. 5, 2017

(65) Prior Publication Data
US 2018/0187018 A1    Jul. 5, 2018

(30) Foreign Application Priority Data
Jun. 30, 2015 (EP) .................................... 15174536

(51) Int. Cl.
| | | |
|---|---|---|
| C09D 11/00 | (2014.01) | |
| C09K 3/00 | (2006.01) | |
| C09D 5/00 | (2006.01) | |
| C09D 4/00 | (2006.01) | |
| C09D 1/00 | (2006.01) | |
| C09C 1/00 | (2006.01) | |
| C09C 1/64 | (2006.01) | |
| A61K 8/19 | (2006.01) | |
| A61K 8/26 | (2006.01) | |
| A61Q 1/02 | (2006.01) | |
| A61K 8/02 | (2006.01) | |
| C09D 7/41 | (2018.01) | |
| C09C 1/24 | (2006.01) | |
| C09D 5/03 | (2006.01) | |
| C09D 11/037 | (2014.01) | |
| C09D 17/00 | (2006.01) | |

(52) U.S. Cl.
CPC .......... *C09C 1/0021* (2013.01); *A61K 8/0254* (2013.01); *A61K 8/19* (2013.01); *A61K 8/26* (2013.01); *A61Q 1/02* (2013.01); *C09C 1/0015* (2013.01); *C09C 1/0081* (2013.01); *C09C 1/24* (2013.01); *C09C 1/642* (2013.01); *C09D 1/00* (2013.01); *C09D 5/035* (2013.01); *C09D 7/41* (2018.01); *C09D 11/037* (2013.01); *C09D 17/007* (2013.01); *A61K 2800/436* (2013.01); *A61K 2800/621* (2013.01); *C01P 2004/20* (2013.01); *C01P 2004/24* (2013.01); *C01P 2004/54* (2013.01); *C01P 2004/61* (2013.01); *C01P 2004/80* (2013.01); *C01P 2006/60* (2013.01); *C01P 2006/62* (2013.01); *C01P 2006/63* (2013.01); *C01P 2006/64* (2013.01); *C01P 2006/65* (2013.01); *C01P 2006/66* (2013.01); *C09C 2200/1054* (2013.01); *C09C 2220/20* (2013.01)

(58) Field of Classification Search
USPC ....................... 106/31.01, 31.13, 31.6, 31.65
See application file for complete search history.

(56) References Cited

U.S. PATENT DOCUMENTS

| | | | |
|---|---|---|---|
| 5,277,711 A | 1/1994 | Schmidt et al. | |
| 2003/0085380 A1* | 5/2003 | Schuhmacher | C09B 67/0098 252/299.7 |
| 2006/0047018 A1 | 3/2006 | Li et al. | |
| 2007/0034112 A1 | 2/2007 | Mronga et al. | |
| 2008/0115693 A1* | 5/2008 | Hashizume | C09C 1/0081 106/404 |
| 2015/0104573 A1* | 4/2015 | Wosylus | C09C 3/063 427/214 |

FOREIGN PATENT DOCUMENTS

| | | |
|---|---|---|
| DE | 4405492 A1 | 8/1995 |
| EP | 0033457 A2 | 8/1981 |
| EP | 0688833 A2 | 5/1995 |
| EP | 0708154 A2 | 4/1996 |
| EP | 1682622 | 7/2006 |
| EP | 1904587 | 4/2008 |
| JP | 54-81337 A | 6/1979 |
| JP | H06-016965 A | 1/1994 |
| JP | 2005-255984 A | 9/2005 |

(Continued)

OTHER PUBLICATIONS

International Search Report dated Sep. 2, 2016, in PCT/EP2016/064993, filed Jun. 28, 2016.

(Continued)

*Primary Examiner* — James E McDonough
(74) *Attorney, Agent, or Firm* — Oblon, McClelland, Maier & Neustadt, L.L.P.

(57) ABSTRACT

The use of an effect pigment (a) comprising an aluminum-based substrate and an iron oxide coating having a red 1st order interference color in combination with a colored absorption pigment (b) for producing a coating having enhanced coloristic properties, in particular enhanced chroma, lightness and hiding power, is provided. The pigment combination of (a) and (b) is suitable for coloring plastics, a fiber, a film and a coating composition such as a paint, a printing ink, a varnish or a powder coating, preferably an automotive, an architectural or an industrial coating composition.

20 Claims, No Drawings

(56) References Cited

FOREIGN PATENT DOCUMENTS

| JP | 2005-264144 A | 9/2005 | |
|---|---|---|---|
| JP | 2015-518910 A | 7/2015 | |
| WO | WO-9529961 A1 * | 11/1995 | ............ C09K 19/00 |
| WO | 96/38505 A1 | 12/1996 | |
| WO | 2005/049739 A2 | 6/2005 | |
| WO | 2013/156327 A1 | 10/2013 | |

OTHER PUBLICATIONS

European Search Report dated Nov. 30, 2015 in Patent Application No. 15 17 4536.1, 2 pages.
W. Ostertag, et al., "Eisenoxidbeschichtete Aluminiumpigmente" Farbe + Lack, vol. 93, Issue 12, Dec. 1987, pp. 973-976.

* cited by examiner

USE OF IRON OXIDE COATED ALUMINUM FLAKES HAVING RED 1st ORDER INTERFERENCE COLOR IN COATINGS

The present invention relates to the use of an effect pigment (a) comprising an aluminum-based substrate and an iron oxide coating having a red $1^{st}$ order interference color in combination with a colored absorption pigment (b) for producing a coating having enhanced coloristic properties, preferably enhanced chroma, lightness and/or hiding power. Further, the invention relates to a pigment combination of said effect pigment (a) and pigment (b) in a specific weight ratio, to an article coated with a composition comprising said pigment combination, and to the use of said pigment combination for coloring plastics, a fiber, a film or a coating composition such as a paint, a printing ink, a varnish or a powder coating, preferably an automotive, an architectural or an industrial coating composition.

Luster or effect pigments are used in many areas, for example in automotive coatings, decorative coatings, plastics, paints, printing inks, and cosmetics.

The optical effect is based on the directed reflection of light at predominantly sheet-like, parallel-oriented, metallic or strongly refractive pigment particles. Depending on the composition of the pigment platelets, there are interference, reflection and absorption phenomena which create angular-dependent color and lightness effects.

Metallic effect pigments are all of platelet-shaped substrates known to the skilled person, examples being aluminum platelets/flakes or metal oxide-coated aluminum platelets/flakes. Platelet-shaped aluminum pigments having a coating of iron oxide are well known and described, e.g., in EP-A-0033457 or by W. Ostertag et al., Farbe and Lack 12 (1987) 973-976. They belong to the class of effect pigments which, by virtue of their particular color properties, have found wide use in the coloration of coatings, paints, printing inks, plastics, ceramic compositions and glazes and cosmetic preparations.

Iron oxide coated aluminum pigments derive their particular optical profile from a combination of specular reflection at the surface of the aluminum platelet, selective light absorption in the iron oxide layer and light interference at the film-like surfaces of the iron oxide layer. Light interference leads to a color which is mainly determined by the thickness of the iron oxide coating layer. Dry pigment powders therefore exhibit the following hues in air with increasing iron oxide layer thickness which are classified as due to $1^{st}$ order or $2^{nd}$ order interference:

$1^{st}$ order interference colors: pale yellow, green-gold, gold, reddish-gold, red, violet, grayish-violet;
$2^{nd}$ order interference colors: yellow, gold, reddish-gold, red-gold, red.

Iron oxide coated aluminum pigments are very bright and opaque, that is why they are widely used in automotive coatings. The pigments customarily used in this field are based on aluminum platelets and exhibit a metallic mirror effect.

Metal oxide layers of effect pigments can be provided on the metallic substrate particles by gas phase decomposition of volatile metal compounds in the presence of oxygen and/or water vapor or by a wet-chemical coating process (e.g., sol-gel or precipitation process).

EP-A-0033457 describes a process for the preparation of colored effect pigments comprising a metallic substrate whose surface is at least partially covered with an iron oxide, wherein iron pentacarbonyl is oxidized to iron oxide in a fluidized bed of the metallic substrates with oxygen at above 100° C.

US-A-2008/0115693 describes colored flake pigments comprising a flaky base material and a pigment bonded to said base material. The base material may be composed of aluminum flakes covered with iron oxide.

US-A-2006/0047018 discloses colored interference pigments having the following structure $Fe_2O_3/SnO_2/[SiO_2/Al(P)]$. They are described as pigments having metallic luster with a reddish color of high chromaticity.

US-A-2007/0034112 discloses luster pigments based on aluminum platelets which are coated with iron oxide by chemical vapor deposition. The aluminum platelets have an average size of from 8 to 30 µm, an average thickness of from 300 to 600 nm and an aspect ratio of from 15 to 70. Pigments are described which, when applied in a coating, exhibit a gold, orange or red interference color.

In wet-chemical preparation methods, metal oxide containing layers can be applied by hydrolytic reaction of appropriate metal salts, e.g. iron(III) salts such as iron(III) chloride and sulfate, or hydrolysable organometallic compounds. Details about the preparation of a metal oxide coating layer on a metal-based substrate of an effect pigment are provided, e.g., in EP-A-0708154 or JP-A-54081337.

WO-A-2013/156327 discloses a wet-chemical preparation process, wherein an initially formed hydroxyl-containing metal oxide layer on an aluminum or aluminum alloy substrate is subjected to a liquid post-treatment medium at a temperature of at least 90° C.

U.S. Pat. No. 5,277,711 discloses a process for preparing a mixture of iron-oxide coated aluminum particles and iron oxide coated particles by coating aluminum and mica particles conjointly with iron oxide by gas phase deposition.

US-A-2015/0104573 discloses a process for preparing a colored effect pigment wherein $SiO_2$ passivated aluminum platelets are coated in an aqueous medium with iron oxide resulting in $2^{nd}$ order interference, followed by adding mica coated with iron oxide to form a homogenous mixture, separating and drying.

Iron oxide coated aluminum pigments are known for brilliant colors in the golden to red color area. Pigments having a golden to reddish-golden (orange) $1^{st}$ order interference color are mainly used in order to provide the corresponding colorations in coating applications, while coating applications in the red color area generally use pigments having a red $2^{nd}$ order interference color. Coatings prepared with those pigments show generally good coloristic properties, like high chroma, high gloss as well as high opacity.

Pigments having a red $1^{st}$ order interference color generally show a brilliant red color shade as a dry powder, however, when applied in coating applications, the coloristic properties are not sufficient for use in such applications. Incorporated in coatings pigments having a red $1^{st}$ order interference color show in full shade lower chroma and a weaker color than as dry powder in air.

Since there is a commercial interest in coating applications of high brilliance, high chroma and high hiding power, there is a continuing need for providing such coatings.

Therefore, it is an object of the present invention to provide a pigment combination comprising an aluminum-based substrate and an iron oxide coating having a red $1^{st}$ order interference color, said pigment combination exhibiting improved coloristic properties in coating applications, like improved chroma, lightness and/or hiding power in coating applications, especially in red-hued or reddish automotive coatings.

A further object of the present invention is to provide an effect pigment comprising an aluminum-based substrate and an iron oxide coating having a red $1^{st}$ order interference color for use especially in coating applications exhibiting enhanced coloristic properties, like improved chroma, lightness and/or hiding power, in particular in red-hued or reddish coating applications.

It has now been found that a pigment combination based on an effect pigment comprising an aluminum-based substrate and an iron oxide coating having a red $1^{st}$ order interference color may be used for producing a coating having the desired properties. The admixture of a further colored absorption pigment especially of a yellow to violet color tone enables a coating having superior coloristic properties compared to a pigment combination comprising the corresponding effect pigment having a $2^{nd}$ order interference color.

Accordingly, in a first aspect the invention relates to the use of an effect pigment (a) comprising an aluminum-based substrate and an iron oxide coating having a red $1^{st}$ order interference color in combination with a colored absorption pigment (b) for producing a coating having enhanced coloristic properties, preferably enhanced chroma, lightness and/or hiding power.

In a further aspect, the invention relates to a process for enhancing the coloristic properties of a coating, especially chroma, lightness and/or hiding power, wherein an effect pigment comprising an aluminum-based substrate and an iron oxide coating having a red $1^{st}$ order interference color is used in combination with a colored absorption pigment.

In a further aspect, the invention relates to a pigment combination comprising
(a) an effect pigment comprising an aluminum-based substrate and an iron oxide coating having a red $1^{st}$ order interference color; and
(b) a colored absorption pigment,
wherein the weight ratio of effect pigment (a) to pigment (b) is of from 95:5 to 5:95, preferably 80:20 to 5:95, more preferably 75:25 to 20:80.

In a further aspect, the invention relates to the use of the pigment combination as defined herein for coloring plastics, a fiber, a film or a coating composition such as a paint, a printing ink, a varnish or a powder coating, preferably an automotive, an architectural or an industrial coating composition.

In a further aspect, the invention relates to an article coated with a composition comprising a pigment combination as defined herein; and to an automotive coating, which is colored with a pigment combination as defined herein.

Color may be described in different color space systems. As used herein, the color data like C* (chroma), h* (hue angle), L* (lightness), a* (red-green axis) and b* (yellow-blue axis) are understood as defined in the CIELAB color measuring system (specified by the Commission Internationale de l'Eclairage). For example, considering a point A in the CIELAB color space, it is defined by the three coordinates L*, a* and b*. The chromaticity coordinates a* and b* may also be expressed by way of cylindrical coordinates C* and h*, as known to one skilled in the art.

The term "opacity" or "hiding power" of a pigmented medium means the capability of the pigmented medium to hide the color or color differences of a substrate which is overcoated.

The term "iron oxide" used herein means α-iron(III) oxide (alpha-iron(III) oxide) in particular. However, the term "iron oxide" also comprises mixtures of α-iron(III) oxide with minor amounts of γ-iron(III) oxide (gamma-iron (III) oxide), magnetite ($Fe_3O_4$), hydrated iron oxide or iron oxide hydroxide (e.g., FeO(OH), $Fe_2O_3.H_2O$, $Fe_2O_3.nH_2O$ with n≥2, $Fe(OH)_3$, $Fe(OH)_2$ or a mixture of two or more of these hydroxyl-containing iron-oxides). Preferably, Fe atoms are present as Fe(III). However, within the present invention Fe atoms may also be present as Fe(II) and/or Fe(IV).

The term "an iron oxide coating having a red $1^{st}$ order interference color" used herein means a coating of iron oxide applied on an optionally passivated aluminum-based substrate. When incorporated in a basecoat a hue angle h* of about 50° to about 60° in the L*C*h* color space according to the CIELAB system is obtained (15° illumination).

The term "colored absorption pigment" used herein means a colored pigment excluding white pigments, like titanium dioxide (C.I. Pigment White 6), or any effect pigment, i.e., pigments which exhibit directed reflection at predominantly two-dimensional, oriented metallic or highly refractive particles, especially metallic platelets, oxide coated metallic platelets and coated mica platelets.

The term "transparent pigment" used herein means a pigment that provides coatings which are substantially transparent in the range of 400 to 700 nm, without appreciable scattering of radiation in such wavelengths.

The term "a mixture thereof" or "a combination thereof" means any possible mixture or combination of two or more components mentioned in the respective list, either of the same or different kind of components.

The pigment combination of the present invention consists of at least two components, wherein the effect pigment (a) comprises an aluminum-based substrate and an iron oxide coating having a red $1^{st}$ order interference color, and the second pigment (b) is at least one colored absorption pigment.

Generally, pigment (b) may be any pigment other than an effect pigment or a white pigment. Pigment (b) may be a pigment ranging from a yellow to violet color tone, preferably a pigment having a similar red color tone than the effect pigment (a). A combination with other colored pigments like a black or brown pigment may also be possible to achieve the effect.

The weight ratio of effect pigment (a) to pigment (b) may be varied in a wide range.

Accordingly, in a preferred embodiment, the present invention relates to the use of an effect pigment (a) comprising an aluminum-based substrate and an iron oxide coating having a red $1^{st}$ order interference color in combination with a colored absorption pigment (b) for producing a coating having enhanced coloristic properties, preferably enhanced chroma, lightness and/or hiding power, wherein the weight ratio of the effect pigment (a) and the pigment (b) is of from 95:5 to 5:95, preferably 80:20 to 5:95, more preferably 75:25 to 20:80.

The effect pigment (a) comprises an aluminum-based substrate and an iron oxide coating having a red $1^{st}$ order interference color, preferably an aluminum flake or platelet and a coating having a red $1^{st}$ order interference color.

Appropriate aluminum-based substrate particles are generally known to the skilled person. The aluminum-based substrate particles may be made of an aluminum core or aluminum alloy core which may be at least partly be coated with one or more passivation layers.

The aluminum or aluminum alloy core is usually in the form of platelets or flakes.

As an exemplary aluminum alloy, aluminum bronze may be mentioned.

The aluminum or aluminum alloy platelets or flakes may be obtained by means of PVD techniques (PVD: Physical Vapor Deposition) or by common atomizing and grinding techniques. Suitable aluminum or aluminum alloy platelets are produced, for example, by the Hall process by wet grinding in white spirit. The starting material is an atomized, irregular aluminum grit which is ball-milled in white spirit and in the presence of lubricant into platelet-shaped particles and subsequently classified.

The substrate is preferably aluminum. The aluminum substrate may be of the "cornflake" type or of the "silver dollar" type depending on the quality and shape of the starting granules and on the milling conditions.

Alternatively, the aluminum flakes may be produced via PVD techniques, also known as VMP (Vacuum Metallized Pigment). Aluminum is coated preferably in vacuum on a plastic foil pre-prepared with a release layer. By dissolving the release layer big aluminum flakes are usually produced which are further classified to the desired particle diameter. The thickness of thus produced flakes is generally about 5 to 100 nm, preferably about 10 to 50 nm. Usually, thus prepared flakes show uniform thickness distribution and high hiding power.

Average thickness and average diameter of aluminum or aluminum alloy platelets or flakes may be varied over a broad range. Typically, the average thickness of the platelets or flakes may be within the range of 5 nm to 1500 nm, preferably 20 to 1000 and the average diameter may be within the range of 5 µm to 100 µm, preferably 8 to 50 µm. Typically, the aspect ratio of average diameter to average thickness may be within the range of 30 to 5000. The diameter may be determined by laser scattering size determinations. The thickness of the platelets or flakes is usually be determined by transmission electron microscopy (TEM) produced on cross-cuts.

As mentioned above, the aluminum or aluminum alloy core of the aluminum-based substrate particles may at least partially be coated with one or more passivation layers.

Appropriate passivating layers are generally known to the skilled person. The passivating layer is preferably an inorganic layer such as a metal phosphate layer, or an inorganic oxide layer. If the inorganic passivating layer is a metal phosphate layer, the metal may be selected from Ti, V, Cr, Mn, Fe, Co, Ni, Cu, Zn, Al, Zr, Nb, Mo, Ta or W. If the inorganic passivating layer is an inorganic oxide layer, the oxide may be selected from Ti, V, Cr, Mn, Fe, Co, Ni, Cu, Zn, Al, Zr, Nb, Mo, Ta, W, Ge, Si, Sn and Bi oxides or any combination thereof.

Preferably, the passivating layer is a metal phosphate layer, a silica layer, an aluminum oxide layer, a hydrated aluminum oxide (AlOOH) layer or a combination thereof.

According to a preferred aspect, the invention relates to the use of the effect pigment (a), wherein the effect pigment (a) comprises an aluminum substrate which is optionally passivated with a layer of a metal phosphate, silica, aluminum oxide, hydrated aluminum oxide or a combination thereof.

Methods for preparing a passivating layer on an effect pigment substrate such as aluminum platelets are generally known to the skilled person.

In principle, a passivating layer may be produced by a wet-chemical method or a chemical vapor deposition (CVD) method. For example, aluminum pigments passivated with a layer of aluminum oxide and/or hydrated aluminum oxide are described in WO-A-96/38505 or WO-A-2005/049739.

In the wet-chemical process, appropriate precursor compounds such as organic silicon and/or aluminum compounds in which the organic groups are bonded to the metals via oxygen atoms are hydrolyzed in the presence of the substrate particles (e.g., aluminum flakes or platelets) and of an organic solvent in which the metal compounds are soluble. Preferably, a metal alkoxide (especially tetraethoxysilane and aluminum triisopropoxide) is hydrolyzed in the presence of an alcohol (e.g. ethanol or isopropanol) and a basic or acid catalyst (e.g. aqueous ammonia and/or amines). This is preferably done by initially charging substrate particles, isopropanol, water and ammonia, heating this mixture to from 40° C. to 80° C., with stirring and continuously adding a solution of the metal alkoxide in isopropanol. Following a subsequent stirring time of usually from 1 to 15 hours, the mixture is cooled down to room temperature, and the coated pigment is isolated by filtering off, washing and optionally drying. Further details about the method of preparing a passivating layer on aluminum are provided, e.g., in EP-A-0708154 and DE-A-4405492.

The iron oxide layer may be produced by a wet-chemical method or a chemical vapor deposition (CVD) method, preferably by CVD. Accordingly, the effect pigment (a) is preferably coated by a chemical vapor deposition process.

The CVD process is advantageously carried out as disclosed in EP-A-0033457 or US-A-2007/0034112 through oxidative decomposition of iron carbonyl in the gas phase in the presence of fluidized substrate particles (e.g., aluminum flakes or platelets). The coating process is generally performed until the desired $1^{st}$ order interference color is obtained. The iron oxide coating has a thickness which results in $1^{st}$ order interference.

The geometric thickness of the iron oxide coating obtainable via CVD process usually is about 35 nm to 45 nm. The geometric layer thickness is usually be determined on the basis of TEM micrographs (cross-cuts).

The wet chemical process may be carried out by hydrolysis of suitable iron compounds, for example, inorganic salts such as iron nitrate, iron sulfate or iron chloride, or, with or without simultaneous oxidation, of other especially organic iron compounds, such as iron acetate, iron formate, iron citrate, iron acetylacetonate and ferrocene, in the presence of substrate particles suspended in water and/or organic solvents and with or without subsequent calcination. The coating process is generally performed until the desired $1^{st}$ order interference color is obtained. The iron oxide coating has a thickness which results in $1^{st}$ order interference.

The geometric thickness of the iron oxide coating obtainable via a wet-chemical process usually is about 80 to about 150 nm. The geometric layer thickness may be determined on the basis of TEM micrographs (cross-cuts).

The present effect pigment may optionally be provided with a surface modification adapted to the particular end-use, wherein the effect pigment is brought into contact with a surface-modifying agent, e.g., with a surface-modifying agent having a functional group which is reactive to the surface of the effect pigment.

For the pigment surface modification step, the effect pigment (a) may be provided in a liquid medium containing at least one surface-modifying agent. However, it is also possible to bring the surface-modifying agent into contact with the effect pigment of a calcination step via the gas phase.

Methods for surface modification of effect pigments and appropriate surface modifying agents such as silanes having surface-reactive functional groups (e.g., alkoxysilanes etc.) are known to the skilled person and may improve compatibility of the effect pigment with the varnish or lacquer. Surface modification methods and agents are described, for example, in EP-A-1682622, EP-A-1904587 and EP-A-0688833.

The second pigment (b) may be any transparent colored absorption pigment of a color tone ranging from yellow to violet dependent on the desired shade of the coating. Suitable pigments (b) may be expressed by their hue angle ranging from about 300° to about 110° (counter-clockwise). A combination with other colored pigments like a black or brown pigment may also be possible, for example, a transparent carbon black pigment or transparent black perylene pigments.

Pigment (b) may be an organic pigment, an inorganic pigment or a mixture thereof. Preferably, pigment (b) has a similar red color tone than effect pigment (a).

Accordingly, in a preferred aspect, pigment (b) is a transparent pigment, especially selected from the group consisting of an organic pigment, an inorganic pigment and a mixture thereof.

Organic colored absorption pigments suitable for the present pigment combination include, for example, a pigment selected from the group consisting of a monoazo, disazo, disazo condensation, anthanthrone, anthraquinone, anthrapyrimidine, benzimidazolone, quinacridone, quinophthalone, diketopyrrolopyrrole, dithioketopyrrolopyrrole, dioxazine, flavanthrone, isoindoline, isoindolinone, isoviolanthrone, metal complex, perinone, perylene, pyranthrone, pyrazoloquinazolone, indigo, thioindigo, triarylcarbonium pigment and a mixture thereof, including a solid solution or a mixed crystal thereof.

Suitable examples include the following:

Monoazo pigments: C.I. Pigment Yellow 1, 3, 62, 65, 73, 74, 97, 183 and 191; C.I. Pigment Orange 5, 38 and 64; C.I. Pigment Red 1, 2, 3, 4, 5, 23, 48:1, 48:2, 48:3, 48:4, 49, 49:1, 51, 51:1, 52:1, 52:2, 53, 53:1, 53:3, 57:1, 58:2, 58:4, 63, 112, 146, 148, 170, 184, 187, 191:1, 210, 245, 247 and 251;

Disazo pigments: C.I. Pigment Yellow 12, 13, 14, 16, 17, 81, 83, 106, 113, 126, 127, 155, 170, 174, 176 and 188; C.I. Pigment Orange 16, 34 and 44;

Disazocondensation pigments: C.I. Pigment Yellow 93, 95 and 128; C.I. Pigment Red 144, 166, 214, 220, 221, 242 and 262;

Anthanthrone pigments: C.I. Pigment Red 168;

Anthraquinone pigments: C.I. Pigment Yellow 147 and 199; C.I. Pigment Red 177;

Anthrapyrimidine pigments: C.I. Pigment Yellow 108;

Benzimidazolone pigments: C.I. Pigment Yellow 120, 151, 154, 180, 181; C.I. Pigment Orange 36 and 72, C.I. Pigment Red 175, 185, 208; C.I. Pigment Violet 32; C.I. Pigment Brown 25;

Quinacridone pigments: C.I. Pigment Orange 48 and 49; C.I. Pigment Red 122, 202, 206 and 209; C.I. Pigment Violet 19;

Quinophthalone pigments: C.I. Pigment Yellow 138;

Diketopyrrolopyrrole pigments: C.I. Pigment Orange 71, 73 and 81; C.I. Pigment Red 254, 255, 264, 270 and 272;

Dioxazine pigments: C.I. Pigment Violet 23 and 37;

Flavanthrone pigments: C.I. Pigment Yellow 24;

Isoindoline pigments: C.I. Pigment Yellow 139 and 185; C.I. Pigment Orange 61 and 69, C.I. Pigment Red 260;

Isoindolinone pigments: C.I. Pigment Yellow 109, 110 and 173;

Isoviolanthrone pigments: C.I. Pigment Violet 31;

Metal complex pigments: C.I. Pigment Red 257; C.I. Pigment Yellow 117, 129, 150, 153 and 177;

Perinone pigments: C.I. Pigment Orange 43; C.I. Pigment Red 194;

Perylene pigments: C.I. Pigment Red 123, 149, 178, 179 and 224; C.I. Pigment Violet 29;

Pyranthrone pigments: C.I. Pigment Orange 51; C.I. Pigment Red 216;

Pyrazoloquinazolone pigments: C.I. Pigment Orange 67 and C.I. Pigment Red 216;

Indigo pigments: C.I. Pigment Red 282;

Thioindigo pigments: C.I. Pigment Red 88 and 181; C.I. Pigment Violet 38;

Triarylcarbonium pigments: C.I. Pigment Red 81, 81:1 and 169; C.I. Pigment Violet 1, 2, 3 and 27;

C.I. Pigment Yellow 101 (Aldazin yellow).

Preferably, the organic pigment is a red-hued organic pigment, for example a red or orange organic pigment selected from an anthraquinone, diketopyrrolopyrrole, isoindolinone, metal complex, perinone, perylene, indigo pigment or any mixture thereof, including a solid solution or a mixed crystal.

Especially preferred are Pigment Yellow 129, Pigment Yellow 110, Pigment Red 168, Pigment Red 177, Pigment Red 179, Pigment Red 282 and any diketopyrrolopyrrole pigment like Pigment Orange 73, Pigment Red 254, Pigment Red 255, Pigment Red 264, Pigment Red 270 or Pigment Red 272.

Suitable organic pigments are, for example, commercially available under the trademarks Irgazin® Cosmoray Orange L 2950, Irgazin Rubine L 4030, Irgazin DPP Orange RA, Irgazin Red L 3630, Irgazin Yellow L 2040, Irgazin Yellow L 0800, Paliogen® Red L 3885 or Paliogen Red L 3920.

Suitable inorganic pigments may be a transparent yellow iron oxide pigment (C.I. Pigment Yellow 42), a transparent red iron oxide pigment (C.I. Pigment Red 101) or a mixture thereof. Especially preferred is a red iron oxide pigment.

Suitable inorganic black or brown pigments may be carbon black (C.I. Pigment Black 7), graphite (C.I. Pigment Black 10) or chrome iron oxide (C.I. Pigment Brown 29).

Suitable inorganic pigments are, for example, commercially available under the trademark Sicotrans®.

The colored absorption pigment (b) is preferably transparent.

Additionally, an opaque colored absorption pigment may be used in small amounts for special effects, generally in an amount less than 10% by weight, preferably less than 5% by weight, based on the weight of all pigments in the composition.

The pigments used herein are preferably present in finely dispersed form. Typically, the organic pigments have an average primary particle size of 200 nm or less, preferably about 80 to 200 nm. The inorganic pigments typically have an average particle size of 200 nm or less, preferably about 80 to 200 nm. The average particle size may be determined according to DIN ISO 13320:2009.

In a further aspect, the invention relates to a pigment combination comprising (a) an effect pigment comprising an aluminum-based substrate and an iron oxide coating having a red $1^{st}$ order interference color; and (b) a colored absorption pigment, wherein the weight ratio of effect pigment (a) to pigment (b) is of from 95:5 to 5:95, preferably 80:20 to 5:95, more preferably 75:25 to 20:80.

Preferably, pigment (b) is a transparent pigment, especially selected from the group consisting of an organic pigment, an inorganic pigment and a mixture thereof.

In particular, the organic pigment is a red-hued organic pigment, for example a red or orange organic pigment selected from an anthraquinone, diketopyrrolopyrrole, isoindolinone, metal complex, perinone, perylene, indigo pigment or any mixture thereof, including a solid solution or a mixed crystal.

The inorganic pigment may be a transparent yellow iron oxide pigment (C.I. Pigment Yellow 42), a transparent red iron oxide pigment (C.I. Pigment Red 101) or a mixture thereof. Especially preferred is a red iron oxide pigment.

The pigment combination may be incorporated into the application system in a customary manner. Usually, pigment (b) is added in a pre-dispersed state. The effect pigment (a) comprising an aluminum-based substrate and an iron oxide coating having a red $1^{st}$ order interference color may be added as a slurry.

The instant pigment combination is outstandingly suitable for all pigment end-use applications, especially coloring organic or inorganic materials of natural and synthetic origin, for example, a) for mass coloring polymers, e.g. in the form of resins, rubber or plastics including films and fibers;
b) for the preparation of paints, paint systems, coating compositions, for example, in automotive, architectural and industrial coating compositions,
c) printing inks, e.g., digital printing like ink-jet printing, as well as for toners in electro-photography, e.g. for laser printers;
d) as an additive to colorants, such as pigments and dyes; and the like.

Paints are aqueous or solvent-borne coating materials and also powder coating materials, in which the instant pigment combination may be employed. Organic film-forming binders that may be used include all of the binders that are usual in the coatings sector. Examples of binder materials which may be colored with the pigment combination of the invention include more particularly:

oil-based materials (based on linseed oil or polyurethane oils),
cellulose-based materials (NC, CAB, CAP),
materials based on chlorinated rubber,
vinyl materials (based on PVC, PVDF, VC copolymer, polyvinyl acetate, polyvinyl ester dispersion, polyvinyl alcohol, polyvinyl acetal, polyvinyl ether, polystyrene, styrene copolymers),
acrylic materials,
alkyd materials,
saturated polyester materials,
unsaturated polyester materials,
polyurethane materials (one pack, two pack),
epoxy materials,
silicone materials.

The systems are described in detail in D. Stoye, W. Freitag, Paints, Coatings and Solvents, Second Edition, 1998, Wiley-VCH.

Preferably, the pigment combination is used in waterborne and solvent-borne coating applications, more preferably in decorative coating compositions like architectural, automotive or industrial coating compositions.

The instant pigment combination is generally incorporated into their respective application media in a customary way. An article may then be coated with these application media thus pigmented. Said article may be, for example, a vehicle body, an industrial equipment, an architectural facing element, etc.

In case of plastics, the instant pigment combination may also be incorporated for coloring into the application medium in the mass. The articles comprise the instant pigment combination.

The pigment combination may be used in an amount of from 0.01 to 75% by weight, preferably 0.01 to 50% by weight, based on the total weight of the material to be colored.

In a further aspect, the invention relates to the use of the pigment combination as defined in any aspect herein-before for coloring or pigmenting plastics, a fiber, a film, a ceramic material or a coating composition such as a paint, a printing ink, a varnish or a powder coating, preferably an automotive, an architectural or an industrial coating composition. The coating composition may be any decorative coating composition like an automotive, an architectural or an industrial coating composition or a paint. The coating composition, printing ink or paint may be waterborne or solvent-borne. Preferably, the pigment combination is used as a colorant for an automotive, architectural, industrial coating composition, a paint, a printing ink or plastics. In particular, the pigment combination is used as a colorant for an automotive OEM or refinish coating composition.

In a further aspect, the invention relates to plastics, a fiber, a film, or a coating composition such as a paint, a printing ink, a varnish or a powder coating, which is colored or pigmented with a pigment combination as defined in any aspect herein-before.

In a further aspect, the invention relates to an article coated with a composition comprising a pigment combination as defined in any aspect herein-before.

Any material of the article may be coated with the composition comprising the instant pigment combination, including such materials as glass, ceramics, plastics, smooth-surfaced composites and metallic substrates. Especially, the composition is particularly adapted for metallic articles or plastic articles. The article may be bare substrate material or, in the case of metal substrates, may be pretreated to impart corrosion resistance as by phosphatizing, or electrocoating like cathodic dip coating, or other similar treatments well known in the art.

A coating comprising the instant pigment combination is especially suitable for a multilayer coating used in the automotive industry. The pigment combination is usually incorporated into the basecoat layer of a basecoat/clearcoat coating system, as known in the art.

Accordingly, the invention relates to an automotive coating, which is colored or pigmented with a pigment combination as defined in any aspect herein-before.

In a further aspect, the invention relates to a process for coloring or pigmenting plastics, a fiber, a film, or a coating composition such as a paint, a printing ink, a varnish or a powder coating, which process comprises adding thereto a pigment combination as defined in any aspect herein-before.

In a further aspect, the invention relates to a process for enhancing the coloristic properties of a coating, especially chroma, lightness and/or hiding power, wherein an effect pigment comprising an aluminum-based substrate and an iron oxide coating having a red $1^{st}$ order interference color is used in combination with a colored absorption pigment.

The pigment combination of the invention is excellent in its coloristic properties, in particular in chroma, lightness and/or hiding power.

The admixture of a colored absorption pigment (b), especially of a yellow to violet color tone, to the effect pigment (a) comprising an aluminum-based substrate and an iron oxide coating having a red $1^{st}$ order interference color enables a coating having superior coloristic properties compared to a similar pigment combination with the corresponding effect pigment having a $2^{nd}$ order interference color. The coatings are more brilliant expressed by a combination of a higher chroma and a higher lightness.

Moreover, the hiding power or opacity is significantly increased. The coloristic properties may be further improved when a colored absorption pigment of similar color tone than the effect pigment having the red $1^{st}$ order interference color is used.

Further, the performance characteristics like weather fastness and light fastness needed for exterior use coatings are not adversely affected.

The definitions and preferences given for the pigment mentioned herein-before apply in any combination as well as in any combination for the other aspects of the invention.

The present invention will now be explained in more detail with reference to the following examples. These examples should not be construed as limited. Unless otherwise stated, "%" is always % by weight.

EXAMPLES

In order to determine the CIELAB values of hue h [°], chroma C* and lightness L*, the coating films obtained (in masstone) are measured as follows: the pigment(s) is/are incorporated by stirring with a level of total pigmentation of 5% by weight (based on the total weight of the wet varnish) into a conventional solvent-borne, medium solids cellulose acetobutyrate (CAB)/polyester varnish (pigment/binder 20/100), until the pigments are finally dispersed. The completed varnish is applied onto aluminum panels with a wet film thickness of about 150 to 160 μm and subsequently dried at room temperature to a thickness of about 20 μm. The color data are determined using a multi-angle colorimeter BYK-MAC (from BYK Gardner) with a constant incident angle of 45°. The values C*, L*, a*, b* and h* are measured at 15° and −15 (relative to the specular angle).

In order to determine the opacity (hiding power), the coating films obtained (in masstone) are measured as follows: The basecoat is sprayed in form of a wedge on a panel with black and white contrasts like a chess game. It is visually determined where the hiding zone starts. At that point the basecoat thickness is determined with a coating thickness gauge (DeFelsko PosiTector 6000).

Synthesis Example 1

In a laboratory fluidized bed reactor 1000 g of aluminum platelets with an average particle size d50=18 μm are fluidized with nitrogen and heated up to 180° C. within 1 hour. After reaching that temperature water vapor and air are dosed with 400 L/h and 150 L/h, respectively. The oxygen content is adjusted to be below 3%. Subsequently, gaseous $Fe(CO)_5$ (produced by heating the liquid material outside the reactor to 60° C.) is dosed with 50 mL/h using a nitrogen stream. The process reaches the desired red color of $1^{st}$ order interference at an amount of around 390 ml of $Fe(CO)_5$. The aluminum content determined by chemical analysis of the product is about 80% by weight, whereas the iron oxide content is about 20% by weight.

Synthesis Example 2

75 g of $SiO_2$ coated aluminum platelets (prepared according to step (a) of Example 1 of EP-A-0708154) are dispersed in 700 mL of water. The suspension is heated to 80° C., and the pH is adjusted to pH≈3. Simultaneously, an aqueous 50% iron nitrate solution and NaOH are added in order to keep the pH constant. The addition is stopped when the color of $2^{nd}$ order orange to red is achieved. The pigment composition according to chemical analysis is $Al:SiO_2:Fe_2O_3$=32:11:57.

Examples 1-4 and Comparative Example 1

A pigment combination comprising Synthesis Example 1 and Paliogen Red L 3885 (C.I. Pigment Red 179) in the following weight ratios is formed:

| (Synthesis Example 1:Pigment Red 179) | |
|---|---|
| Comparative Example 1 | 100:0 |
| Example 1 | 90:10 |
| Example 2 | 70:30 |
| Example 3 | 50:50 |
| Example 4 | 30:70 |

Comparative Examples 2-7

A pigment combination comprising Synthesis Example 2 and Paliogen Red L 3885 in the following weight ratios is formed:

| (Synthesis Example 2:Pigment Red 179) | |
|---|---|
| Comparative Example 2 | 100:0 |
| Comparative Example 3 | 90:10 |
| Comparative Example 4 | 70:30 |
| Comparative Example 5 | 50:50 |
| Comparative Example 6 | 30:70 |

The results are demonstrated in Tables 1 to 3.

TABLE 1

| Examples | h | C* | L* | a* | b* | Δh* | ΔC* | ΔL* | ΔE* |
|---|---|---|---|---|---|---|---|---|---|
| Observation angle −15° | | | | | | | | | |
| Comp. Ex. 2 | 56.68 | 127.6 | 94.48 | 70.08 | 106.6 | | | | |
| Comp. Ex. 1 | 56.92 | 123.6 | 104.5 | 67.46 | 103.6 | 0.5 | −4 | 10 | 10.8 |
| Observation angle 15° | | | | | | | | | |
| Comp. Ex. 2 | 53.97 | 117.6 | 87.67 | 69.18 | 95.12 | | | | |
| Comp. Ex. 1 | 56.42 | 114.0 | 96.61 | 63.61 | 95.00 | 5 | −3.6 | 8.9 | 10.8 |

TABLE 2

| Example | h | C* | L* | a* | b* | Δh* | ΔC* | ΔL* | ΔE* |
|---|---|---|---|---|---|---|---|---|---|
| Observation angle −15° | | | | | | | | | |
| Comp. Ex. 3 | 51.03 | 130.4 | 80.52 | 82.00 | 101.4 | | | | |
| Example 1 | 50.95 | 126.2 | 88.87 | 79.48 | 97.97 | −0.2 | −4.2 | 8.3 | 9.4 |
| Comp. Ex. 4 | 46.88 | 114.7 | 62.65 | 78.39 | 83.72 | | | | |
| Example 2 | 46.30 | 118.0 | 71.28 | 81.52 | 85.31 | −1.2 | 3.3 | 8.6 | 9.3 |
| Comp. Ex. 5 | 43.56 | 100.9 | 51.52 | 73.1 | 69.52 | | | | |
| Example 3 | 44.06 | 110.7 | 60.31 | 79.53 | 76.97 | 0.9 | 9.8 | 8.8 | 13.2 |
| Comp. Ex. 6 | 39.53 | 83.35 | 41.99 | 64.29 | 53.05 | | | | |
| Example 4 | 40.76 | 92.82 | 48.58 | 70.31 | 60.6 | 1.9 | 9.8 | 6.6 | 11.7 |
| Observation Angle 15° | | | | | | | | | |
| Comp. Ex. 3 | 49.23 | 121.6 | 74.25 | 79.4 | 92.09 | | | | |
| Example 1 | 50.53 | 116.6 | 81.67 | 74.13 | 90.02 | 2.7 | −5 | 7.4 | 9.3 |
| Comp. Ex. 4 | 45.7 | 108.8 | 58.21 | 76.00 | 77.88 | | | | |
| Example 2 | 45.92 | 109.9 | 65.45 | 76.42 | 78.91 | 0.4 | 1 | 7.2 | 7.3 |
| Comp. Ex. 5 | 42.81 | 96.41 | 47.79 | 70.73 | 65.51 | | | | |
| Example 3 | 43.66 | 103.1 | 55.06 | 74.58 | 71.17 | 1.5 | 6.7 | 7.3 | 10.0 |
| Comp. Ex. 6 | 39.28 | 80.27 | 38.65 | 62.13 | 50.81 | | | | |
| Example 4 | 40.58 | 87.25 | 44.11 | 66.27 | 56.76 | 1.9 | 7 | 5.5 | 9.1 |

A difference of 1 unit in C* may already be recognized by a person skilled in the art.

TABLE 3

Thickness of a hiding basecoat layer

| Example | |
|---|---|
| Comp. Ex. 3 | 19-21 μm |
| Example 1 | 15-17 μm |
| Comp. Ex. 4 | 25-27 μm |
| Example 2 | 21-23 μm |
| Comp. Ex. 5 | 34-36 μm |
| Example 3 | 22-24 μm |
| Comp. Ex. 6 | 42-44 μm |
| Example 4 | 35-38 μm |

The smaller the values in μm the higher the hiding power.

The invention claimed is:

1. A method for producing a coating having an enhanced coloristic property, the method comprising:
   coating an article with an effect pigment (a) and a colored absorption pigment (b),
   wherein the effect pigment (a) comprises an aluminum-based substrate and an iron oxide coating having a red 1$^{st}$ order interference color,
   the colored absorption pigment (b) comprises an organic transparent pigment, an inorganic transparent pigment, or both, where the organic transparent pigment is at least one red-hued pigment selected from the group consisting of an anthraquinone pigment, a diketopyrrolopyrrole pigment, an isoindolinone pigment, a metal complex pigment, a perylene pigment, and an indigo pigment,
   a weight ratio of the effect pigment (a) to the colored absorption pigment (b) is from 95:5 to 5:95, and
   the effect pigment (a) and the colored absorption pigment (b) are in a dispersed form.

2. The method according to claim 1,
   wherein the weight ratio of the effect pigment (a) to the colored absorption pigment (b) is from 90:10 to 30:70.

3. The method according to claim 1,
   wherein the colored absorption pigment (b) is the organic transparent pigment and is a perylene pigment.

4. The method according to claim 1, wherein the colored absorption pigment (b) is the inorganic transparent pigment and is a yellow or red iron oxide.

5. The method according to claim 1,
   wherein the effect pigment (a) is coated by a chemical vapor deposition process.

6. The method according to claim 1,
   wherein the effect pigment (a) comprises an aluminum substrate which is optionally passivated with a layer of a metal phosphate, silica, aluminum oxide, hydrated aluminum oxide or a combination thereof.

7. The method according to claim 1,
   wherein the coating is an automotive coating, an architectural coating or an industrial coating.

8. A process for enhancing a coloristic property of a coating, comprising:
   contacting an effect pigment (a) and a colored absorption pigment (b) in the coating,
   wherein the effect pigment (a) comprises an aluminum-based substrate and an iron oxide coating having a red 1$^{st}$ order interference color,
   the colored absorption pigment (b) comprises an organic transparent pigment, an inorganic transparent pigment, or both, where the organic transparent pigment is at least one red-hued pigment selected from the group consisting of an anthraquinone pigment, a diketopyrrolopyrrole pigment, an isoindolinone pigment, a metal complex pigment, a perylene pigment, and an indigo pigment,
   a weight ratio of the effect pigment (a) to the colored absorption pigment (b) is from 95:5 to 5:95, and
   the effect pigment (a) and the colored absorption pigment (b) are in a dispersed form.

9. A pigment combination, comprising:
   (a) an effect pigment comprising an aluminum-based substrate and an iron oxide coating having a red 1$^{st}$ order interference color; and
   (b) a colored absorption pigment comprising an organic transparent pigment, an inorganic transparent pigment, or both, where the organic transparent pigment is at least one red-hued pigment selected from the group consisting of an anthraquinone pigment, a diketopyrrolopyrrole pigment, an isoindolinone pigment, a metal complex pigment, a perylene pigment, and an indigo pigment, wherein a weight ratio of the effect pigment (a) to the colored absorption pigment (b) is from 95:5 to 5:95, and the effect pigment (a) and the colored absorption pigment (b) are in a dispersed form.

10. The pigment combination according to claim 9, wherein the weight ratio of the effect pigment (a) to the colored absorption pigment (b) is from 90:10 to 30:70.

11. A method for coloring an article, comprising:

contacting the article with the pigment combination according to claim 9, wherein the article is a plastic, a fiber, a film or a coating composition.

12. An article coated with a composition comprising the pigment combination of claim 9.

13. An automotive coating, comprising:

the pigment combination of claim 9.

14. The method according to claim 1, wherein the method is suitable for enhancing chroma, lightness and/or hiding power.

15. The method according to claim 1, wherein the weight ratio of the effect pigment (a) to the colored absorption pigment (b) is from 75:25 to 20:80.

16. The method according to claim 3, wherein the organic transparent pigment is in the form of a solid solution or a mixed crystal.

17. The method according to claim 11, wherein the coating composition is a paint, a printing ink, a varnish or a powder coating.

18. The pigment combination according to claim 9, wherein a weight ratio of the effect pigment (a) to the colored absorption pigment (b) is from 90:10 to 30:70, and the colored absorption pigment (b) is the organic transparent pigment and is a red perylene pigment.

19. The method according to claim 1, wherein the coating has enhanced chroma, lightness and/or hiding power as compared to a coating produced by a method comprising coating the article with an effect pigment having an orange $2^{nd}$ order interference color and the colored absorption pigment (b).

20. The method according to claim 1, wherein the effect pigment (a) consists of a pigment having the aluminum-based substrate and the iron oxide coating having the red 1st order interference color.

* * * * *